United States Patent [19]

Hasham et al.

[11] Patent Number: 5,680,876
[45] Date of Patent: Oct. 28, 1997

[54] FLOSS BRUSH MANUFACTURE AND PRODUCT

[75] Inventors: Amin Hasham, San Jose; Robert E. Tricca, Danville, both of Calif.

[73] Assignee: Gillette Canada Inc., Kirland, Canada

[21] Appl. No.: 457,256

[22] Filed: Jun. 1, 1995

[51] Int. Cl.$^6$ .................................................. A61C 15/00
[52] U.S. Cl. .......................... 132/329; 132/323; 132/321
[58] Field of Search ........................... 132/329, 321, 132/323, 324, 328, 325

[56] References Cited

U.S. PATENT DOCUMENTS

| | | | |
|---|---|---|---|
| 2,667,443 | 1/1954 | Ashton | 167/93 |
| 3,337,412 | 8/1967 | Elbreder | 132/329 |
| 3,516,846 | 6/1970 | Matson | 117/36.2 |
| 3,516,941 | 6/1970 | Matson | 252/316 |
| 3,578,545 | 5/1971 | Carson et al. | 161/86 |
| 3,755,064 | 8/1973 | Maierson | 161/174 |
| 3,771,536 | 11/1973 | Dragan | 132/89 |
| 3,778,383 | 12/1973 | Schibler et al. | 252/316 |
| 3,800,812 | 4/1974 | Jaffe | 132/89 |
| 3,830,246 | 8/1974 | Gillings | 132/89 |
| 3,837,351 | 9/1974 | Thornton | 132/89 |
| 3,896,824 | 7/1975 | Thornton | 132/89 |
| 3,897,795 | 8/1975 | Engel | 132/89 |
| 3,943,949 | 3/1976 | Ashton et al. | 132/89 |
| 4,008,727 | 2/1977 | Thornton | 132/89 |
| 4,019,522 | 4/1977 | Elbreder | 132/90 |
| 4,029,113 | 6/1977 | Guyton | 132/91 |
| 4,033,365 | 7/1977 | Klepak et al. | 132/89 |
| 4,087,376 | 5/1978 | Foris et al. | 252/316 |
| 4,089,802 | 5/1978 | Foris et al. | 252/316 |
| 4,100,103 | 7/1978 | Foris et al. | 252/316 |
| 4,142,538 | 3/1979 | Thornton | 132/89 |
| 4,162,688 | 7/1979 | Tarrson et al. | 132/92 A |
| 4,251,386 | 2/1981 | Saeki et al. | 252/316 |
| 4,360,514 | 11/1982 | Buck | 424/56 |
| 4,362,712 | 12/1982 | Buck | 424/49 |
| 4,403,089 | 9/1983 | Buck | 528/247 |
| 4,414,990 | 11/1983 | Yost | 132/91 |
| 4,419,396 | 12/1983 | Sugimoto | 428/40 |
| 4,528,226 | 7/1985 | Sweeny | 428/40 |
| 4,548,219 | 10/1985 | Newman et al. | 132/91 |
| 4,576,190 | 3/1986 | Youssef | 132/89 |
| 4,627,975 | 12/1986 | Lynch | 424/49 |
| 4,638,823 | 1/1987 | Newman et al. | 132/91 |
| 4,646,766 | 3/1987 | Stallard | 132/91 |
| 4,817,643 | 4/1989 | Olson | 132/329 |
| 4,911,927 | 3/1990 | Hill et al. | 424/443 |
| 4,952,392 | 8/1990 | Thame | 424/58 |
| 5,113,880 | 5/1992 | Honda et al. | 132/321 |
| 5,153,254 | 10/1992 | Chen | 524/505 |
| 5,284,169 | 2/1994 | Gillegan et al. | 132/321 |
| 5,334,646 | 8/1994 | Chen | 524/474 |
| 5,353,820 | 10/1994 | Suhonen et al. | 132/321 |

FOREIGN PATENT DOCUMENTS

| | | | |
|---|---|---|---|
| 0172671 | 2/1986 | European Pat. Off. | A61C 15/04 |
| 2002830 | 2/1979 | United Kingdom . | |
| 2258402 | 2/1993 | United Kingdom | A61C 15/04 |
| WO 91/08792 | 6/1991 | WIPO | A61M 31/00 |
| WO 93/02633 | 2/1993 | WIPO | A61C 15/00 |

*Primary Examiner*—Gene Mancene
*Assistant Examiner*—Pedro Philogene
*Attorney, Agent, or Firm*—Chester Cekala

[57] ABSTRACT

Dental floss brushes, as described herein, are extremely difficult to coat with wax coatings. When conventional waxes are utilized, the floss brush becomes matted and gummy. We have developed an improved wax coating solution which results in a thin, uniform coating with good adhesion characteristics. This invention relates to an improved floss brash product and to a novel process for its manufacture. In particular this invention is directed to an improved floss brash made of a textured, high tenacity nylon yarn which provides the scraping functions of a floss under high tension and the brushing functions of a yarn under low tension. The present yarns require a wax coating to improve lubricity during use. The present product exhibits a uniform, thin wax coating. The present process imparts a thin coating by utilizing a "viscosity lowering agent" in the wax coating solution.

33 Claims, 2 Drawing Sheets

FLOSS BRUSH MANUFACTURE AND PRODUCT

1. Field of the Invention

This invention relates to an improved floss brush product and to a novel process for its manufacture. In particular this invention is directed to an improved floss brush made of a textured; high tenacity nylon yarn which provides the scraping functions of a floss under high tension and the brushing functions of a yarn under low tension. The present yarns require a wax coating to improve lubricity during use. The present product exhibits a uniform, thin wax coating. The present process imparts a thin coating by utilizing a "viscosity lowering agent" in the wax coating solution.

2. Background of the Invention

Tooth decay and dental disease can be caused by bacterial action resulting from the formation of plaque about the teeth and/or the entrapment of food particles between the teeth and interstices therebetween. The removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended. The term "dental floss", as used herein, is defined to include both dental flosses, dental tapes and any similar article.

To improve the effectiveness and convenience of dental flosses, dental flosses combining a thin "floss" portion and a thickened "brush" portion, together with a threader have been developed. The brush portion, when drawn between tooth surfaces, has been found to provide an improved cleaning action which removes materials left by the floss portion, when used alone. The combination provides a substantially superior cleaning action. Such devices are described in U.S. Pat. No. 4,008,727, for example. The complexity of this product requires that each floss segment be individually manufactured and that the product be packaged as bundles of the individual, separate floss articles.

A continuous yarn having brush segments separated by thinner segments is disclosed in U.S. Pat. No. 4,152,538. However, products formed using conventional textured nylon yarns and previously developed manufacturing processes were not satisfactory. Manufacture of brush floss products of this type involves applying a polymer solution to the yarn. The solvent is then selectively evaporated from the thinned segment portion while avoiding solvent evaporation from the brush portion, the yarn being maintained under high tension during this procedure. The solvent in the brush portion is then removed while the yarn is relaxed, that is, under low or no tension.

Attractive and pleasant flavors and flavor odors have been provided in dental products to impart a flavor to the flosses and encourage their regular use. These have been applied in the form of flavoring oils to the surface of floss or wax coating on the floss, or dispersed in wax coatings applied to the floss. Wax-coated floss brushes result in a thick wax coating which clogs and mats the brush filaments.

In a process described in commonly assigned U.S. Pat. No. 5,353,820, flavoring particles are applied to a floss brush. The flavoring particles are said to be retained without significant loss through evaporation or from oxidation.

In a process described in commonly assigned U.S. Pat. No. 5,284,169, heated liquid polyethylene glycol esters of beeswax are used to coat floss brushes. Unfortunately, this process failed to achieve consistent, reproducibly thin coatings, even when excess wax is removed prior to cooling.

OBJECTS AND SUMMARY OF INVENTION

It is one object of this invention to provide a floss brush with a thin wax coating with good adhesion properties.

It is another object of this invention to provide a wax coated floss brush made from a teared yarn which retains substantially all of the bulk and thickness of the original, uncoated, relaxed yarn.

It is still a further object of this invention to provide an improved floss brush which can be spooled and dispensed as a continuous brush/thread from a traditional floss dispenser.

It is further an object of the present invention to provide an improved wax coating solution which results in a thin wax coat on floss brushes.

These and other objects will be evident from the following:

Dental floss brushes, as described herein, are extremely difficult to coat with wax coatings. When conventional waxes are utilized, the floss brush becomes matted and gummy. This is undoubtedly due to the thick wax coating which results. Applicants have developed an improved wax coating solution which results in a thin, uniform coating with good adhesion characteristics. This improved coating includes a "viscosity lowering agent."

In one embodiment, the floss brush is coated with a low melting wax composition in combination with an orally acceptable flavoring oil, silicone oil, hydrocarbons (e.g., isoeicosane) or mixtures thereof having a Brookfield viscosity of from about 1 to about 30 centipoise (cp), preferably from 5 to 15 cp, when measured at 70° C.

In summary, one process of this invention is a process for manufacturing a continuous length of dental floss brush comprising alternating sequences of thread portions and floss brush portions integral therewith. The process comprises the steps of:

(a) coating a reverse twisted high tenacity nylon yarn with a solution of polymer in a volatile solvent, the polymer being selected from the group consisting of nylon, polyurethane and mixtures there;

(b) selectively vaporizing solvent from thread portions of the yarn while preventing significant vaporization of solvent from brush portions of the yarn, while the yarn is maintained under a tension of less than 1N;

(c) steam treating the brush portions of the yarn while the yarn is under a tension of approximately zero until the brush portions of the yarn have regained at least about 100 percent of the diameter of the uncoated, relaxed yarn; and (d) removing residual solvent from the thread portion and/or brush portions of the yarn while the yarn is under a tension of approximately zero.

(e) coating the threads of the brush portion of the product of step (d) with a solution of wax combined with a viscosity lowering agent without clogging the openings thereof.

The wax coating solution can be applied as a liquid (preferably at an elevated temperature of from above about 60° up to 80° C.). When elevated coating bath temperatures are used, the coated brush portions are subsequently cooled to a temperature below 50° C. The wax solution is preferably a microcrystalline wax plus a viscosity lowering amount of a "viscosity lowering agent" selected from the group consisting of orally acceptable flavoring oils, silicone oils, hydrocarbons or mixtures thereof. The wax solution can be used alone or in combination with other conventional wax additives, e.g., solvents, surfactants, active ingredients, sweeteners, antioxidants, additional flavorants, or mixtures thereof.

A preferred process of this invention for producing a wax coated nylon yarn with unclogged openings comprises: coating the yarn with a solution comprised of wax combined with a viscosity lowering agent at a temperature of from about 60° to about 80° C. (most preferably at 70°); and cooling the coated yarn to a temperature below about 50° C. The solution can optionally contain solvents, surfactants, active ingredients, sweeteners, antioxidants, additional flavorants, or mixtures thereof.

The products of these processes are also aspects of this invention.

DETAILED DESCRIPTION OF THE INVENTION

The elongate teeth cleaning article of this invention provides the combined functions of an interproximal brush and floss. In the representation shown in FIG. 1, the polymer coated thin floss brush 2 comprises a brush portion which is imparted with a thin coating of wax 4 positioned over the entire length. The brush is relaxed and yarn-like, suitable for cleaning between the teeth in a brushing action, pulling the floss back and forward across tooth and gingival surfaces. The cavities in the brush surface capture and remove food bacteria and other materials on the tooth and gum surfaces. Under tension, the brush portion stretches to become a thread, suitable for the upward and downward scraping motion along the opposed tooth surfaces and facilitates easier insertion between interstitial spaces. When relaxed, the brush portion returns to the yarn-like extended configuration.

Figure 1:
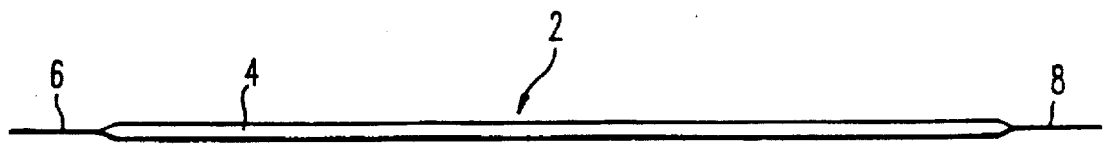
FIG. 1 is a representation of the relaxed dental floss brush of this invention.
Figure 2:
FIG. 2 is a representation of a continuous length of relaxed, connected dental floss brushes of this invention.

The thin floss brush 2 is manufactured in a continuous length of alternating thread and brush portions, a portion of which is shown in FIG. 2. By severing the thread portion 10 separating a terminal thread and brush portion 12, a length of floss corresponding to FIG. 1 is obtained. This continuous length of floss is suitable for dispensing from a spool in a conventional floss dispenser.

Figure 3:
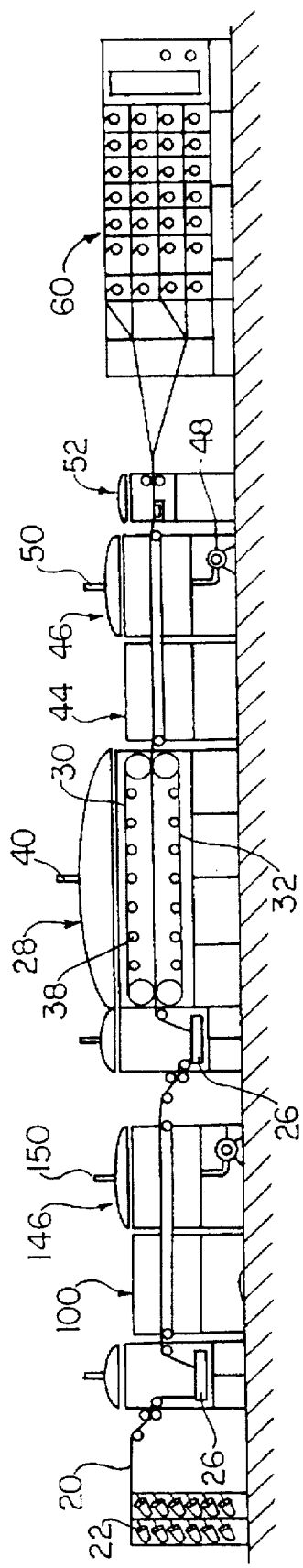
FIG. 3 is a schematic representation of the system for producing a continuous length of connected dental floss brushes of this invention.

FIG. 3 is a schematic representation of the system for producing a continuous length of connected dental floss brushes of this invention. The article is manufactured by processing a yarn, preferably a high tenacity nylon yarn, with a polymer coating, evaporating solvent from the thread portions under tension, steam treating the relaxed yarn, removing excess solvent and evaporating residual solvent, and coating the yarn with a warm solution of a low melting, non-clogging wax combined with a viscosity lowering agent. Optionally, excess wax could be removed after the coating step. Also, a volatile viscosity lowering agent could be used. The product is then collected on reels (spools or cones) which are further processed through a packaging operation to provide the finished output product. Alternatively, the polymer coated yarn can be stored on reels prior to the wax coating operation (See FIG. 5).

Yarn 20 is drawn from yarn packages (spools or cones) which is mounted on a creel 22. Yarn 20 is pulled through the coating bath 126. In coating bath 126, a dye-containing polymer in a volatile solvent is applied to a selected segment of the yarn while the tension is increased, effecting liquid penetration of the yarn while avoiding excessive liquid pickup.

The coated yarn is then transported under tension on to an infrared drying chamber 100. The drying chamber is equipped with a hooded 150 ventilation chamber 146. This chamber is equipped with blower 148.

Yarn 20 is pulled through the second coating bath 26. In coating bath 26, a polymer solution in a volatile solvent is applied to the yarn while the tension is increased, effecting liquid penetration of the yarn while avoiding excessive liquid pickup. Any excess coating solution may be removed by conventional squeeze rollers.

Figure 4:
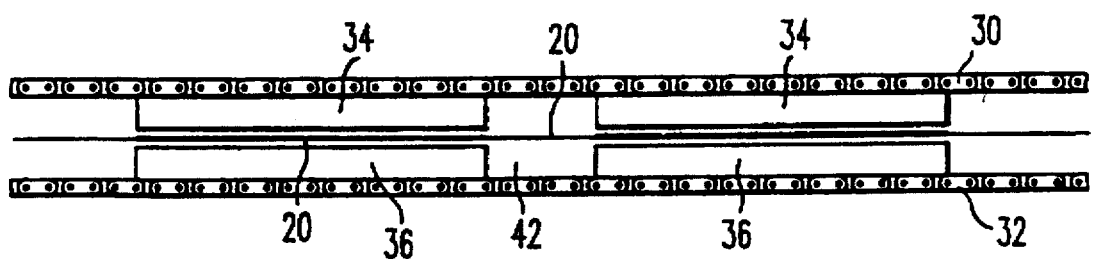
FIG. 4 is a schematic representation of a portion of the drier and heater assembly shown in FIG. 3.

The coated, dyed yarn is then pulled into a chain driven drying chamber 28. Referring to FIGS. 3 and 4, this system comprises opposed moving chains 30 and 32, the opposing faces of each moving chain having respective insulating pads 34 and 36. The upper chain sections include infrared heaters housed in a stainless steel vestibule. The lower chain section includes an air exhaust vestibule. The combination of the forced convection and radiant heat evaporates solvent which is removed from the driving chamber through the air exhaust vestibule 40. The potions of the yarn suspended between and shielded by adjacent insulating pad pairs in heating zones 42 are exposed to the heat, and the exposed coating is completely dried and hardened (the solvent is substantially vaporized) by the time it reaches the exit of the drying chamber. The exposed, dried portions retain the thin configuration formed under tension, producing the thread portion. The portions of the yarn held between the insulating pads 34 and 36 are protected from the heat and experience little or no solvent loss during the period of high tension. The infrared heaters are designed and arranged to provide drying temperatures of from about 70° to 160° C.

The yarn is then passed under relaxed conditions (i.e., low or zero tension) into a steam treatment chamber 44. When the yarn tension is relaxed after emerging from the heater section 28, these undried portions partially contract to a partially bulked configuration. In steam chamber 44, the brush portions are exposed to substantially saturated steam having a temperature within the range of from 80° to 105° C. until the brush portions almost completely contract and substantially regain the original puffiness and bulked condition of the initial uncoated, relaxed yarn. This is usually achieved by a treatment of 3 seconds and longer, depending upon the nature and level of coating.

The rebulked, steam-treated floss is then passed into roller driven drying chamber 46. The residual liquid (solvent and water) is evaporated by conduction and convection heat transfer using heated air having a temperature within the range of from 150° to 200° C. and a flow rate of 150 to 300 cfm. Air is supplied through manifold 50 and vapors are removed through exhaust system 48. The continuous length of floss brush can be collected on reels as an unwaxed floss product at this stage.

For producing a waxed floss brush according to the present invention, the solvent-free floss is passed through a wax coating bath 52 where a wax solution comprised of a wax combined with a "viscosity lowering agent" is applied. Preferably, the solution is at an elevated temperature of from about 60° C. to about 80° C., most preferably 70° C. Optionally, excess wax coating is removed by passing the floss brush between squeeze rollers or the like. The wax coated product is then collected on reels (spools or cones) in the collecting station 60. The floss brush is then rewound from the spools or cones onto conventional individual dispenser spools. The wax coating can also be applied by any method known to those skilled in the art, e.g., spraying, dip coating, roller coating, etc.

When a volatile viscosity lowering agent is used, the viscosity lowering agent may be flashed off and the continuous length of floss brush is passed into a refrigeration or cooling station. Alternately, the floss can be passed through a gas stream produced by a blower where excess solvents are evaporated and the vapors removed through and exhaust manifold.

The steaming process increased bulk of the yarn, yielding a product which slips easily between teeth under tension and which bulks up to be used either as a floss, cleaning by scraping up and down, or by linear movement as a brush. The bulked portion is easier on the gums. The product can accept liquid or solid flavoring materials because of its open mesh structure and increased surface area over regular floss. This provides a product with a more lasting flavor and increased customer appeal.

Preferably, reverse or false twisted, high tenacity nylon yarn having a breaking strength of at least about 5N, preferably above 20N and optimally above 35N was found to be satisfactory. These yarns are formed by first texturizing a high tenacity nylon yarn using a conventional pin-twisting process, using only sufficient heat required for the texturizing and avoiding temperatures which will significantly damage the yarn and its filaments and reduce their strength. Left and right pin-twisted strands are then combined to form the final reverse-twisted, textured yarn product. A suitable yarn is available from Chapman Fraser & Co. Ltd. Thurmaston, Leicester, England.

A preferred high tenacity textured yarn consists of five folds of 110 dtex type 112 Nylon 66 high tenacity yarn with a total of 170 strands, manufactured by ICI Americas. The yarn has the following characteristics:

| | |
|---|---|
| Decitex: | 550 ± 5% |
| Diameter: | 1.5 ± 5% |
| Crimp Rigidity: | 16% ± 3% |
| Tenacity: | 61 cN/tex (Minimum) |
| Breaking Strength: | 36 ± 3 N |
| Loops Free: | 1 per 20 meters (Maximum) -- Defined as one or more folds removed from the main body of yarn giving the distinct appearance of a loop. |
| Knot Free: | zero knots per creel. -- Defined as physical joint in yarn. |
| False Twist: | (ZS X 2)(Z X 1) |
| Twist: | S twist, 78 twists per meter. |

Of course, other methods of forming the floss brush can be utilized in the present invention. See for example, U.S. Pat. No. 4,277,297 to Thornton, issued Jul. 7, 1981, incorporated herein by reference in its entirety. Also, the number of filaments within the brush can vary. Preferably, the filament count its from about 100 to 600 filaments.

The most preferred dental floss brush yarn of this invention is typically made from a reverse twisted, high tenacity nylon yarn. It comprises at least two thread sections having diameters, in their relaxed state, of less than 2.5 mm preferably less than 1.35 min. The thread sections are separated by a floss brush section integral therewith of yarn having a diameter of from 2 to 4 mm, preferably from 2.4 to 3.5 mm, in its relaxed state and a diameter of from 1.7 to 3.0 mm under a tension of 0.05N (newtons). The brush floss has a breaking strength of at least 5N and preferably above 20N. Optimally, the yarn has a breaking strength of at least 35N; the thread sections have diameters, in their relaxed state, of less than 50 percent of the diameter of relaxed, uncoated yarn from which they were formed; the floss brush has, in its relaxed state, at least 100 and preferably at least 220 percent of the original diameter of relaxed, uncoated yarn from which it was formed; and each floss brush section has a diameter under a tension of 0.05N of at least 60 percent, preferably above 75 percent, and optimally above 150 percent of the relaxed uncoated yarn from which it was formed.

The polymer solution applied in coating bath 26 can be a solution or emulsion of a nylon, polyurethane or mixtures thereof. Suitable nylon solutions in lower alkanols of the types conventionally used in coating dental flosses are suitable. An example is the GENTAL™ alkanolic nylon solutions (General Plastics Corporation, Bloomfield, N.J.). Preferred polyurethanes are water dispersible urethanes such as the anionic colloidal urethane elastomer dispersions sold under the tradename SPENSOL® polyurethane dispersions (Spencer-Kellog Products). Optimally, the coating solution or emulsion is a mixture of from 5 to 15 percent of alkanol-soluble nylon and from 5 to 15 percent water-dispersible polyurethane in a mixed water/alkanol solution such as a water/ethanol solution and 25 wt % of SPENSOL® L54 aqueous polyurethane dispersion.

Figure 5:
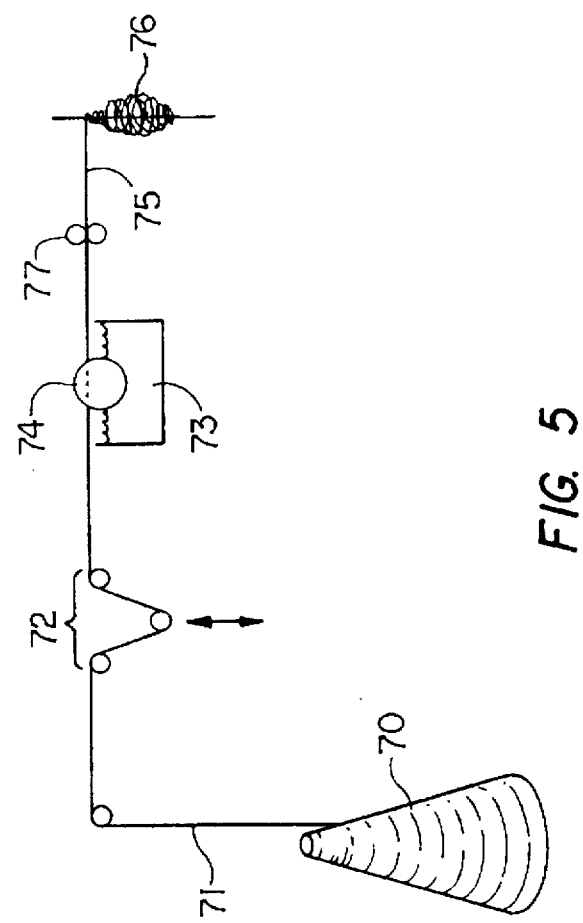
FIG. 5 is a schematic representation of the wax coating system of the present invention.

FIG. 5 is a schematic representation of a creel to bobbin coating operation as used in the present invention. A creel 70 of texturized yarn 71 is positioned at the base of the coater apparatus. The texturized yarn 71 is feed through a tensioner 72 and then to a capillary coater 74 positioned in the wax solution coating bath 73. The bath contains a solution comprising of a wax or wax-like lubricant combined with a sufficient amount of a "viscosity lowering agent" to produce a viscosity of 1–30 cp under the bath temperature conditions. Optionally, the coated yarn could then pass through a pinch roller 77 to remove excess wax coating solution. The final yarn 75 is afforded sufficient time to set the wax solution to a handleable degree prior to storage on a bobbin 76.

In a most preferred embodiment, the wax coating solution is carefully metered onto the yarn so that no wax removal step is necessary. Also, in another embodiment of the present invention a volatile viscosity lowering agent may be flashed off after the wax coating solution is applied.

WAX COATING SOLUTION

Application of conventional microcrystalline waxes or polyethylene glycol waxes to nylon floss brush yarns clog the spaces of the yarn and make it ineffective for use as a brush. We have discovered, however, that waxes combined with a particular viscosity lowering agent can be used to coat such yarns, only the individual filaments of the yarn are coated and most of the original yarn texture and cleaning ability is retained.

As used herein, the "wax" can be any substance that will adhere to the surface of the floss and which will decrease the coefficient of friction of the floss and enable the floss to slide better around the tooth and between the tooth and gums. Waxes will adhere to the surface of floss to a high degree. Polyvinyl alcohol and polyethylene glycol will also adhere to the surface of floss and function like waxes according to the present invention. If the coating substance itself will not sufficiently lower the coefficient of friction, it can carry an additive which will lower the coefficient of friction. The objective is to adhere a material to the floss surface so that the coefficient of friction can be lowered to a desired level to improve the handling characteristics.

In this regard waxes are effective. A variety of waxes can be used. This includes naturally occurring and synthetic waxes. Petroleum derived waxes, such as paraffin should have a melting point of greater than about 50° C. The wax should not be brittle at room temperature. (Note: Additives may be applied to the wax to make it less brittle). These latter requirements negate the use of some waxes. Waxes that melt at less than about 50° C. can become molten during product storage and cause the wax on the floss strands to flow. This could result in problems in dispensing the floss from the rolls. In addition, if the wax is brittle the wax will crack and become removed from the floss during processing and packaging, and later during dispensing and handling prior to usage. Thus, essentially any wax can be used as long as it has a melting point greater than about 50° C. and the wax is not brittle at room temperature, i.e., about 25° C. It also should not be tacky at room temperature.

In the preferred embodiments of the invention, the friction coating is a microcrystalline wax. Microcrystalline waxes are well known in the art. The preferred microcrystalline waxes have a molecular weight of about 500 g/mole to about 900 g/mole and preferably about 600 g/mole to about 800 g/mole. Such microcrystalline waxes have a melting point of about 50° C. to about 100° C. and preferably about 60° C. to about 80° C. Alternative coating materials may include for example a water soluble coating such as polyvinyl alcohol, polyethylene oxidide, polyethylene oxide modified waxes (like Estol) or mono-, di- and triglycerides. These can also be used in addition to a wax coating. The friction lowering coating may be any coating material that is able to adhere to the floss to lower the coefficient of friction.

Microcrystalline waxes which can be used in the present invention include those sold under the tradenames Ultraflex (top 65.6° C.), Victory (top 78.9° C.), Be Square 175 (top 83.9° C.), Starwax (top 85.6° C.), Be Square 185 (mp 87.8° C.), Be Square 195 (top 92.2° C.), Petrolite C-700 (top 92.2° C.), and Petrolite C-1035 (top 93.3° C.) by Petrolite Corporation of Tulsa, Okla. Other microcrystalline waxes which may be used include, for example, those sold by Boler Petroleum Company of Wayne, Pa. under the tradename Bowax 1018 (top 68.3° C.), Mekon White (mp 93.3° C.), Forrex (mp 96.1° C.), and by Shell Oil Company under the tradenames Microcrystalline Wax LMP, MMP or HMP. The preferred microcrystalline waxes are sold by Shell Oil Company under the tradename LMP have a melting point of from 63° to 88° C.

The molecular weights of waxes are calculated as the average of the molecular weights of their hydrocarbon constituents. Paraffin waxes are mainly composed of normal acrylic hydrocarbons and can frequently be characterized by their average molecular weights. It is more difficult to determine the molecular weight of the microcrystalline waxes which typically contain substantial amounts of secondary and tertiary acrylic hydrocarbon isomers and/or cyclid hydrocarbons. There is not necessarily a direct correlation between melting point and molecular weight of the microcrystalline waxes. Nevertheless, lower melting microcrystalline waxes generally have lower molecular weights.

According to the present invention, the wax coating solution is characterized by providing a thin, uniform coating onto the brush section of a bushy floss product. Unfortunately, the above mentioned "waxes" produce a relatively thick coating that tends to gum up the filaments of a brush floss. These coatings also have a tendency of scraping off the brush floss easily. This even occurs at elevated temperatures.

We have discovered that an improved coating can be achieved by lowering the viscosity of the wax coating solution. Preferably, the wax coating solution viscosity is lowered from about 1 to about 30 cp as measured on a Brookfield® viscometer using a number 1 spindle at 70° C. Most preferably the viscosity is from about 2 to about 20 cp and especially from about 5 to about 15 cp.

The viscosity lowering effect is produced by utilizing a viscosity lowering agent. As used herein, the term "viscosity lowering agent" means any chemically inert, orally acceptable material having a viscosity lowering effect on the wax. Optionally, these materials may be volatile having a boiling point below 30° C. Preferred viscosity lowering agents are selected from the group consisting of silicone oils, flavor oils, hydrocarbons and combinations thereof. An amount of these viscosity lowering agents which result in a viscosity lowering of the coating solution to a Brookfield® viscosity of from 1–30 cp at 70° C. is used. It has been observed that small amounts of low viscosity lowering agents are required to achieve a wax solution viscosity according to the present invention while, alternatively, larger amounts of viscosity lowering agents with relatively high viscosities are used.

Suitable viscosity lowering "silicone oils" which can be used in the present invention include "Silicone 244", "Silicone 345" or "Silicone 200" brand cyclomethicones manufactured by Dow Corning.

Suitable viscosity lowering "flavor oils" which can be used in the present invention include mint flavor TP 2850 manufactured by Quest International.

Suitable Viscosity lowering "hydrocarbons" include "Permethyl 99A" brand isododecane, "Permethyl 101A" brand isohexadecane or "Permethyl 102A" brand isoeicosane, all manufactured by Permethyl Corp. Isoeicosane is most preferred.

Also, other conventional wax additives can be included in the wax. For example, the wax can contain wetting agents, like PEG 40 hydrogenated castor oil, Cremaphor brand mfg. by BASF, antioxidants, like tri(nonyphenyl) phosphite, BHT, BHA, TBHQ sweeteners, like saccharin and saccharin acid, aroma masking compounds, handling improvers, surfactants, like glyceryl oleate, and combinations thereof.

Optionally, active components which may be incorporated within the wax include hydrogen peroxide or peroxide producing components such as PVP $H_2O_2$ or Carbamide $H_2O_2$. Fluoride, tooth acidulating agents such as buffered or acidulated phosphofluoride, sodium monofluorophosphate, sodium fluoride, stannous fluoride, plaque control agents, tartar control agents, antibiotics to treat pyorrhea and gingivitis, teeth whitening and bleaching agents, pH buffering agents, antifungal agents, remineralizing agents, hemostatic antibacterials such as benzothonium chloride, acetyl trimethyl ammonium bromide, sanguinaria, triclosan (nonionic), tetracycline, cetyl pyridinium chloride, chlorhexidine and benzothonium chloride. Gantrez resins are a product of GAF Corporation. Additional active components include vitamins, such as Vitamin A, surfactants and flavors including anise, peppermint, wintergreen, spearmint, fruit flavors and the like. Among the pharmacological active agents which may be included are, for example, anti-cancer agents, stimulants, bone growth agents, antigens, hormones, steroids, anti-inflammatory agents and analgesic agents. In a further embodiment, the active agent may be a coagulant to inhibit any bleeding which may be produced by flossing. Although the flosses of the present invention are less prone to cause bleeding than the conventional dental flosses, some bleeding may occur when the user has sensitive gingival tissue. Preferably, the coagulant is mixed in the wax coating so as to directly contact the gum tissue. The coagulants may include vitamin K, calcium ions in the form of water-soluble calcium salts and blood factors that initiate the coagulation cascade. It is possible to incorporate other coagulants from solution in finely dispersed form in the wax coating medium. Alternatively, the coagulants may be solubilized in non-toxic solvents, such as ethanol, polyethylene terepthalate, or diethyl ether. A preferred carrier for this purpose is a water-soluble type of resin, such as polyethylene glycol having an average molecular weight from about 4000 to about 6000 g/mole. The coagulating agents may be applied to the wax coating during or after the initial wax coating has dried. Additional active agents may include, for example, aminocaproic acid, tranexamic acid, adrenaline, alum, noradrenaline, iron salts, zinc salts and calcium alginate.

In further embodiments, dentally acceptable agents such as a cooling agent, for example, menthol and analogues such as N-ether-p-methane-3-carboxamide may be incorporated with the wax to help the patient to detect where the treatment has been applied. The floss may further incorporate colorant agents or fluorescent dye to identify residual plaque deposits, such as, for example, FD&C Red 3 and FD&C Red 4. Polishing agents such as hydrated amorphous silica, hydrated alumina, and colcium carbonate may be applied to the wax.

The viscosity lowering agents also provide a suitable vehicle for applying additional flavoring to the floss brush. They also function as emulsifiers and surfactants and can be combined with alkanolic or aqueous solutions of sweeteners such as saccharine, cyclamates or xylitol and with additional lubricants.

Preferred coating compositions are shown below.

| Example 1 Wax Coating Solution* | | |
|---|---|---|
| | Ingredient | % w/w |
| Lubricant | Microcrystalline Wax LMP | 25.65 |
| Viscosity Lowering Agent | Isoeiconsane [Permethyl 102A] | 23.50 |
| Improves Handling Slip | Glyceryl Oleate | 23.50 |
| Viscosity Lowering Agent | Silicone 244 Fluid [Cyclomethicone] | 23.50 |
| Odor Mask | Flavorant [Masking] | 2.50 |
| Wetting Agent | PEG 40 Hydrogenated Castor Oil | 1.00 |
| Sweetener | Saccharin Acid | 0.25 |
| Antioxidant | Tri(nonylphenyl) phosphite [TNPP] | 0.10 |
| | | 100.00 |

*The above wax coating solution has a Brookfield ® viscosity of 7–8 cp at 70° C.

The above wax coating solution is applied at a temperature of 70° C. and coats evenly through the entire network of filaments. This results in a floss brush which glides well as it wets out in the mouth of the user.

| Example 2 Flavored Wax Coating Solution* | | |
|---|---|---|
| | Ingredient | % w/w |
| Flavor Oil | Mint Flavor | 30.00 |
| Lubricant | Microcrystalline Wax LMP | 29.65 |
| Improved Handling Slip | Glyceryl Oleate | 26.30 |
| Viscosity Lower Agent | Isoeicosane [Permethyl 102A] | 13.30 |
| Sweetener | Saccharin Acid | 0.65 |
| Antioxidant | Tri(nonylphenyl) phosphite [TNPP] | 0.10 |
| | | 100.00 |

*The above flavored wax coating solution has a Brookfield ® viscosity of 7–8 at 70° C.

The above wax coating solution is applied at 70° C. and coats evenly through the entire network of filaments. This results in a floss brash which glides well as it wets out in the mouth of the user.

Although preferred embodiments of the subject invention have been described in some detail, it is understood that obvious variations can be made without departing from the spirit and the scope of the invention as defined by the appended claims.

What is claimed is:

1. A process for manufacturing a wax coated dental floss brush comprising the steps of:
   (a) providing a floss brush yarn; and
   (b) coating the threads of said floss brush with a solution of wax combined with a viscosity lowering agent, wherein said solution has a viscosity of from about 1 to about 30 cp at 70° C.

2. A method according to claim 1 wherein said solution has a viscosity of from about 2 to about 20 when measured at 70° C.

3. A method according to claim 2 wherein said viscosity lowering agent is selected from the group consisting of orally acceptable silicone oils, flavor oils, hydrocarbons and combinations thereof.

4. A method according to claim 3 wherein said silicone oil is cyclomethicone.

5. A method according to claim 3 wherein said flavor oil is a mint flavor.

6. A method according to claim 3 wherein said hydrocarbon is selected from the group consisting of isododecane, isohexadecane, isoeicosane or mixtures thereof.

7. A method according to claims 4, 5 or 6 wherein said solution has a viscosity of from about 5 to about 15 when measured at 70° C.

8. A method according to claim 3 wherein said coating step is performed at from about 60° C. to about 80° C.

9. A method according to claim 8 wherein said coating step is performed at about 70° C.

10. A method according to claim 8 further comprising the following step:
    (c) cooling the coated gain to a temperature below about 50° C.

11. A method according to claim 8 wherein said viscosity lowering agent is volatile.

12. A method according to claim 9 further comprising the following step:
    (c) cooling the coated yarn to a temperature below about 50° C.

13. A method according to claim 12 wherein said yarn is a reverse or false twisted, high tenacity nylon yarn having a breaking strength of at least about 5N.

14. A method according to claim 13 wherein said yarn is a reverse twisted, textured, high tenacity nylon yarn having a breaking strength of at least about 20N.

15. A method according to claim 14 wherein said yarn has a filament count of from about 100 to about 600.

16. A method according to claim 15 wherein said wax is a microcrystalline wax.

17. A method according to claim 16 wherein said microcrystalline wax has a melting point greater than about 50° C.

18. A method according to claim 15 wherein said wax is selected from the group consisting of polyvinyl alcohol, polyethylene oxide, polyethylene oxide modified waxes, monoglycerides, diglycerides, triglycerides and mixtures thereof.

19. A process for manufacturing a wax coated, continuous length of dental floss brush comprising alternating sequences of thread portions and floss brush portions integral therewith, comprising the steps of:

(a) coating a reverse twisted high tenacity nylon yarn with a solution of polymer in a volatile solvent, the polymer being selected from the group consisting of nylon, polyurethane and mixtures there;

(b) selectively vaporizing solvent from thread portions of the yarn while preventing significant vaporization of solvent from brush portions of the yarn, while the yarn is maintained under a tension of less than 1N;

(c) steam treating the brush portions of the yarn while the yarn is under a tension of approximately zero until the brush portions of the yarn have regained at least about 100 percent of the diameter of the uncoated, relaxed yarn;

(d) removing residual solvent from the brush portions of the yarn while the yarn is under a tension of approximately zero; and (e) coating the threads of the brush portion of the product of step (d) with a solution of wax combined with a viscosity lowering agent without clogging the openings thereof; wherein said solution has a viscosity of from 1 to 30 cp at 70° C.

20. A floss brush coated with a solution comprised of a wax and a viscosity lowering agent, wherein said solution has a viscosity of from about 1 to about 30 cp at 70° C.

21. A method according to claim 20 wherein said solution has a viscosity of from about 2 to about 20 when measured at 70° C.

22. A method according to claim 21 wherein said viscosity lowering agent is selected from the group consisting of orally acceptable silicone oils, flavor oils, hydrocarbons and combinations thereof.

23. A method according to claim 22 wherein said silicone oil is cyclomethicone.

24. A method according to claim 22 wherein said flavor oil is a mint flavor.

25. A method according to claim 22 wherein said hydrocarbon is selected from the group consisting of isododecane, isohexadecane, isoeicosane or mixtures thereof.

26. A method according to claims 23, 24 or 25 wherein said solution has a viscosity of from about 5 to about 15 when measured at 70° C.

27. A method according to claim 22 wherein said viscosity lowering agent is volatile.

28. A method according to claim 27 wherein said yarn is a reverse or false twisted, high tenacity nylon yarn having a breaking strength of at least about 5N.

29. A method according to claim 28 wherein said yarn is a reverse twisted, textured, high tenacity nylon yarn having a breaking strength of at least about 20N.

30. A method according to claim 29 wherein said yarn has a filament count of from about 100 to about 600.

31. A method according to claim 30 wherein said wax is a microcrystalline wax.

32. A method according to claim 31 wherein said microcrystalline wax has a melting point greater than about 50° C.

33. A method according to claim 29 wherein said wax is selected from the group consisting of polyvinyl alcohol, polyethylene oxide, polyethylene oxide modified waxes, monoglycerides, diglycerides, triglycerides and mixtures thereof.

* * * * *